(12) United States Patent
Sugiura

(10) Patent No.: US 8,598,870 B2
(45) Date of Patent: Dec. 3, 2013

(54) MAGNETIC RESONANCE IMAGING APPARATUS

(75) Inventor: Satoshi Sugiura, Otawara (JP)

(73) Assignees: Kabushiki Kaisha Toshiba, Minato-Ku, Tokyo (JP); Toshiba Medical Systems Corporation, Otawara-Shi, Tochigi-Ken (JP)

(*) Notice: Subject to any disclaimer, the term of this patent is extended or adjusted under 35 U.S.C. 154(b) by 659 days.

(21) Appl. No.: 12/781,975

(22) Filed: May 18, 2010

(65) Prior Publication Data

US 2010/0308823 A1 Dec. 9, 2010

(30) Foreign Application Priority Data

Jun. 8, 2009 (JP) ................................. 2009-137303
Mar. 25, 2010 (JP) ................................. 2010-070753

(51) Int. Cl.
*G01V 3/00* (2006.01)

(52) U.S. Cl.
USPC .......................................... 324/306; 600/413

(58) Field of Classification Search
USPC ........................... 324/306, 307, 309; 600/413
See application file for complete search history.

(56) References Cited

U.S. PATENT DOCUMENTS

| | | | |
|---|---|---|---|
| 5,857,970 A * | 1/1999 | Purdy | 600/413 |
| 6,501,979 B1 * | 12/2002 | Manning et al. | 600/413 |
| 6,771,999 B2 * | 8/2004 | Salla et al. | 600/413 |
| 6,922,580 B2 * | 7/2005 | DeMeester et al. | 600/413 |

FOREIGN PATENT DOCUMENTS

JP     2-224740     9/1990

OTHER PUBLICATIONS

Bernstein et al., "Handbook of MRI Pulse Sequences", Chapter 12 Physiologic Gating, Triggering, and Monitoring, p. 448.

* cited by examiner

*Primary Examiner* — Louis Arana
(74) *Attorney, Agent, or Firm* — Nixon & Vanderhye PC

(57) ABSTRACT

A magnetic resonance imaging apparatus includes an electrocardio information acquisition unit which acquires a magnetic resonance signal (e.g., showing a cardiac beat) for estimating an electrocardiogram signal of an object in sync with a biomedical signal other than an electrocardiogram signal. A time difference is determined between the electrocardiogram signal and a synchronous position of the biomedical signal as estimated from the acquired magnetic resonance signal. An image data generation unit acquires a magnetic resonance signal for imaging corresponding to a specific time phase of the cardiac cycle in sync with the biomedical signal based on the time difference, to generate an image data corresponding to the specific time phase of the cardiac cycle.

10 Claims, 5 Drawing Sheets

MAGNETIC RESONANCE IMAGING APPARATUS

CROSS-REFERENCE TO RELATED APPLICATIONS

This application claims the benefit of priority of Japanese Patent Application No. 2009-137303, filed Jun. 8, 2009, and No. 2010-070753, filed Mar. 25, 2010, the entire contents of which are incorporated herein by reference.

FIELD

Embodiments described herein generally relate to a magnetic resonance imaging apparatus.

BACKGROUND

Magnetic resonance imaging (MRI) is an imaging procedure which reconstructs an image from an MR (magnetic resonance) signal generated by magnetically exciting the nuclear spin of an object placed in a static magnetic field with an RF signal of Larmor frequency.

In order to obtain an image at a specific time phase of the cardiac cycle using an MRI apparatus, it is necessary to execute a pulse sequence at a predetermined timing synchronizing synchronized with an ECG (electro cardiogram) waveform obtained from a patient as an object to be imaged, and to perform image reconstruction from the acquired echo signal.

However, in order to obtain the ECG waveform, it is necessary to attach an electrode for detecting the ECG signal to the object in advance of imaging, and therefore, time and labor are required.

In addition, for acquiring suitable ECG signals, it is necessary to adjust the fixing point of the electrode, depending on an individual object. Further, because of a noise that is induced to an ECG waveform under the influence of switching of the gradient magnetic field in imaging, an ECG synchronous imaging sometimes cannot be performed appropriately, and image quality may be deteriorated.

In ECG synchronous imaging, an RF pulse for imaging is applied to the object, while the electrode is attached to the object. Thus, the RF pulse is induced to a loop formed with a signal line for transmitting the ECG waveform, a human body, and an electrode, and there is a danger that the object may be injured with a burn. Such a problem becomes remarkable especially for the high magnetic field MRI apparatus with a large electric power of the RF pulse.

From such a background, instead of detecting an EGG signal from an object, a peripheral pulse gating (PPG) method has been developed. In the PPG method, a sensor is attached to a part of the object, such as a finger, a tiptoe, or an earlobe, and a peripheral pulse signal (a PPG signal) of the object is detected by the sensor to image the object in sync with the peripheral pulse signal.

According to this PPG method, it is not necessary to attach an ECG electrode to an object. Therefore, the problem that a suitable synchronization becomes difficult by disorder of an ECG waveform in a gradient magnetic field is also resolved. In addition, heat generation of an electrode in a MRI apparatus using high magnetic field can also be prevented.

However, it should be noted that, while the imaging by the PPG method is performed in sync with cardiac beats, there exists a certain time delay of the peripheral pulse signal from the actual heart stroke. This time delay is dependent on conditions, such as distance between a detection position of the peripheral signal and the heart, and rigidity of a blood vessel.

Therefore, in a conventional imaging method using simply a peripheral pulse signal, image data corresponding to a specified time phase of the cardiac cycle cannot be obtained, while the artifact resulting from cardiac beat can be reduced.

More specifically, the imaging condition for acquiring data in the specific time phase of the cardiac cycle cannot be determined, before imaging. Further, even after imaging, it cannot be determined which image data corresponds to the specified phase of the cardiac cycle.

Thus, a method has been developed, in which both an ECG signal and a PPG signal are acquired from an object, then, a time delay of the PPG signal to the ECG signal is measured, and then, a cardiac time phase is specified from a PPG signal using the measured time delay.

However, in the method of acquiring both an ECG signal and a PPG signal from an object, while matching of an ECG signal and a PPG signal can be performed, an ECG signal still needs to be acquired. Therefore, the problem that the time and effort are required to attach an electrode for detection of an ECG signal to an object still remains. Further, there still exists the danger that the object may be injured with a burn, resulting from induction of the RF pulse to a loop formed with a signal line for transmitting an ECG waveform, a human body and an electrode.

DETAILED DESCRIPTION

According to one embodiment, a magnetic resonance imaging apparatus includes an electrocardio information acquisition unit and an image data generation unit. The electrocardio information acquisition unit acquires a magnetic resonance signal for estimating an electrocardiogram signal of an object in sync with a biomedical signal other than an electrocardiogram signal. The biomedical signal is acquired from the object and shows a cardiac beat. The electrocardio information acquisition unit further determines a time difference between a position of a reference wave of the electrocardiogram signal and a synchronous position of the biomedical signal. The position of the reference wave is estimated from the acquired magnetic resonance signal. The image data generation unit acquires a magnetic resonance signal for imaging corresponding to a specific time phase of the cardiac cycle in sync with the biomedical signal based on the time difference, to generate image data corresponding to the specific time phase of the cardiac cycle from the acquired magnetic resonance signal for imaging.

An embodiment of the magnetic resonance imaging apparatus will be described in detail with reference to the accompanying drawings.

(Configuration and Operation)

Figure 1:
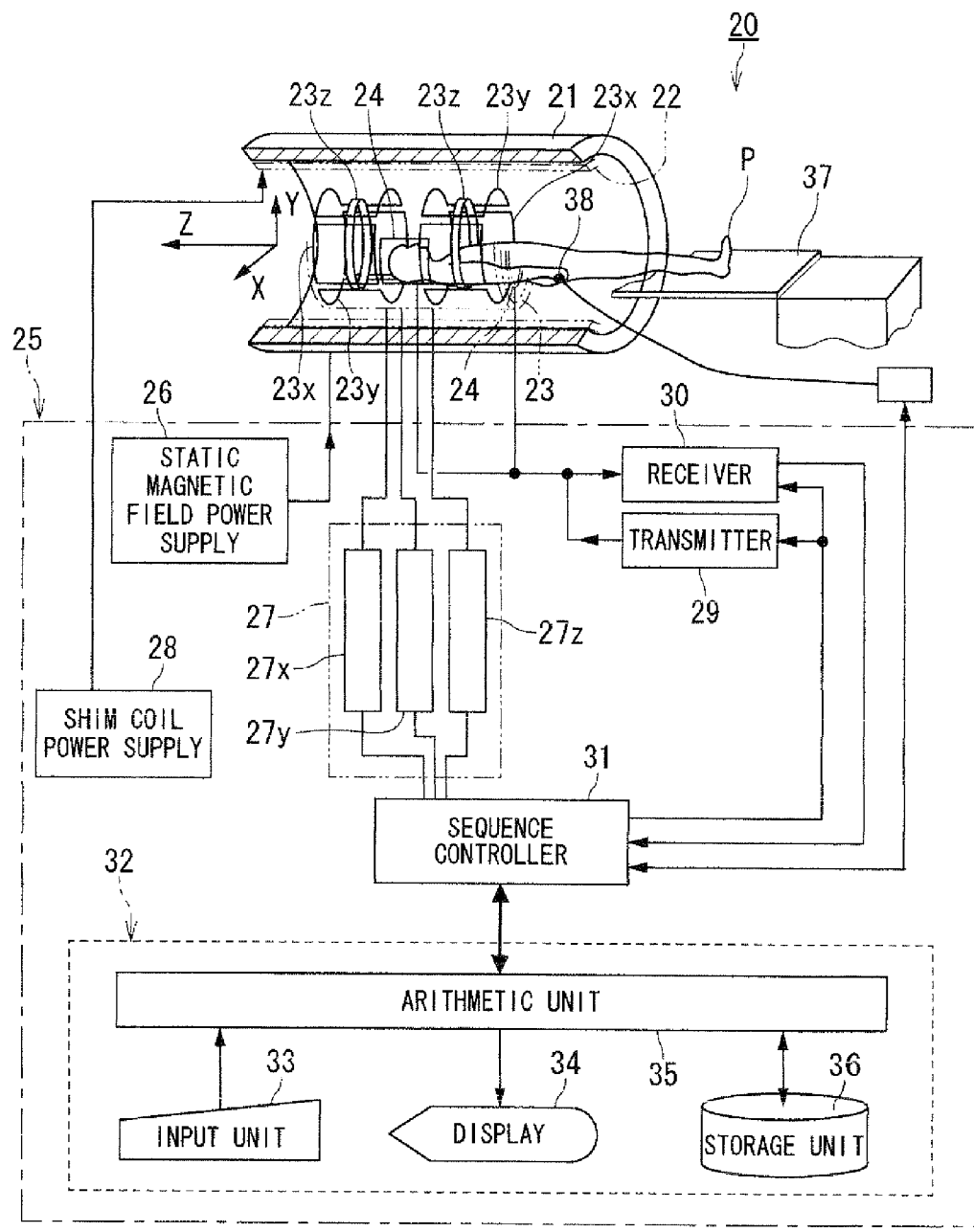
FIG. 1 shows an example of a configuration of the magnetic resonance imaging apparatus according to an embodiment of the present invention.

FIG. 1 is a block diagram showing a configuration of the embodiment of the magnetic resonance imaging apparatus.

The magnetic resonance imaging apparatus 20 is provided with a cylindrical static-magnetic-field magnet 21 which forms a static magnetic field, a shim coil 22 inside the static-magnetic-field magnet 21, a gradient coil 23, and an RF coil 24. The magnetic resonance imaging apparatus 20 is also provided with control system 25.

The control system 25 is provided with a static magnetic field power supply 26, a gradient magnetic field power supply 27, a shim coil power supply 28, a transmitter 29, a receiver 30, a sequence controller 31, and a computer 32.

The gradient magnetic field power supply 27 of the control system 25 includes a X-axis gradient magnetic field power supply 27x, a Y-axis gradient magnetic field power supply 27y, and a Z-axis gradient magnetic field power supply 27z.

The computer 32 is provided with an input unit 33, a display 34, an arithmetic unit 35, and a storage unit 36.

The static-magnetic-field magnet 21 is connected to static magnetic field power supply 26, and forms a static magnetic field in an imaging region by the current supplied from static magnetic field power supply 26. The static-magnetic-field magnet 21 is build up with a superconductive coil in many cases. The static-magnetic-field magnet 21 is connected to the static magnetic field power supply 26 and current is supplied therefrom for magnetization. After static-magnetic-field magnet 21 is magnetized, the static-magnetic-field magnet 21 is usually disconnected from the static magnetic field power supply 26. The static-magnetic-field magnet 21 may be build up with a permanent magnet, and for this case, the static magnetic field power supply 26 is not needed.

Alternatively, the static-magnetic-field magnet 21 may be build up with a permanent magnet, and for this case, the static magnetic field power supply 26 is not needed.

Inside the static-magnetic-field magnet 21, a coaxial and cylindrical shim coil 22 is provided. The shim coil 22 is connected to a shim coil power supply 28, and equalizes a static magnetic field by the current supplied from the shim coil power supply 28.

The gradient coil 23 includes X-axis gradient coil 23x, Y-axis gradient coil 23y, and Z-axis gradient coil 23z, and is formed in a cylindrical shape inside of the static-magnetic-field magnet 21.

Bed 37 is provided inside the gradient coil 23, and the inside of the gradient coil corresponds to an imaging region. Object P is laid on the bed 37.

The RF coil 24 includes a local coil for receiving provided near the bed 37 or the object P, a whole body coil (WBC) for receiving/transmitting provided in the gantry, and so forth.

The gradient coil 23 is connected with gradient magnetic field power supply 27. The X-axis gradient coil 23x, the Y-axis gradient coil 23y, and the Z-axis gradient coil 23z of the gradient coil 23 are connected with a X-axis gradient magnetic field power supply 27x, a Y-axis gradient magnetic field power supply 27y, and a Z-axis gradient magnetic field power supply 27z of the gradient magnetic field power supply 27, respectively.

With the current supplied to X-axis gradient coil 23x, Y-axis gradient coil 23y, and Z-axis gradient coil 23z, respectively from X-axis gradient magnetic field power supply 27x, Y-axis gradient magnetic field power supply 27y, and Z-axis gradient magnetic field power supply 27z, the gradient magnetic field Gx of an X axial direction, gradient magnetic field Gy of Y axial direction, and gradient magnetic field Gz of Z axial direction are formed in an imaging region, respectively.

The RF coil 24 is connected with a transmitter 29 and/or a receiver 30. A transmitting RF coil 24 transmits an RF signal sent from the transmitter 29 to the object P. On the other hand, a receiving RF coil 24 receives a NMR signal generated from the nuclear spin in the object P due to excitation by the RF signal, and sends the NMR signal to the receiver 30.

The sequence controller 31 of control system 25 is connected with the gradient magnetic field power supply 27, the transmitter 29, and the receiver 30.

The sequence controller 31 has a function to memorize sequence information in which control information, such as strength of pulse current, applying period, applying timing, etc., necessary to drive a gradient magnetic field power supply 27, transmitter 29, and receiver 30 is described.

The sequence controller 31 also has a function to generate X-axis gradient magnetic field Gx, Y-axis gradient magnetic field Gy, Z-axis gradient magnetic field Gz, and an RF signal, by driving the gradient magnetic field power supply 27, the transmitter 29, and the receiver 30 according to the memorized predetermined sequence.

The receiver 30 detects and A/D (analog to digital) converts the NMR signal to generate raw data, which are complex data. The sequence controller 31 receives the raw data from the receiver 30 and then sends the raw data to the computer 32.

The transmitter 29 sends an RF signal to the RF coil 24 based on the control information received from the sequence controller 31. As mentioned above, the receiver 30 generates the raw data which is the digitized complex data, by detecting the NMR signal received from RF coil 24, and performing the necessary signal processing and carrying out the A/D conversion. Then, the receiver 30 sends the raw data to the computer 32.

The magnetic resonance imaging apparatus 20 is further equipped with a peripheral pulse sensor 38 which acquires the PPG signal as an example showing a signal of a cardiac beat of the object P1. The PPG signal is a peripheral pulse signal for synchronization which shows change of the blood flow volume according to the cardiac cycle. A peripheral pulse is detected as an optical signal at a part of the object P, such as a fingertip, a tiptoe, and an earlobe. Thus, the peripheral pulse sensor 38 is attached to an arbitrary part of object P, such as a fingertip, a tiptoe, and an earlobe.

The peripheral pulse sensor 38 detects reflected light obtained by irradiating infrared light on the skin, transforms the detected reflected light into an electrical signal, and outputs the electrical signal as a PPG signal to the computer 32 via the sequence controller 31.

The computer 32 carries out various functions by executing programs saved in the storage unit 36 of computer 32 with arithmetic unit 35. The magnetic resonance imaging apparatus 20 may alternatively carry out the various functions using not the stored programs, but specific electronic circuits.

Figure 2:
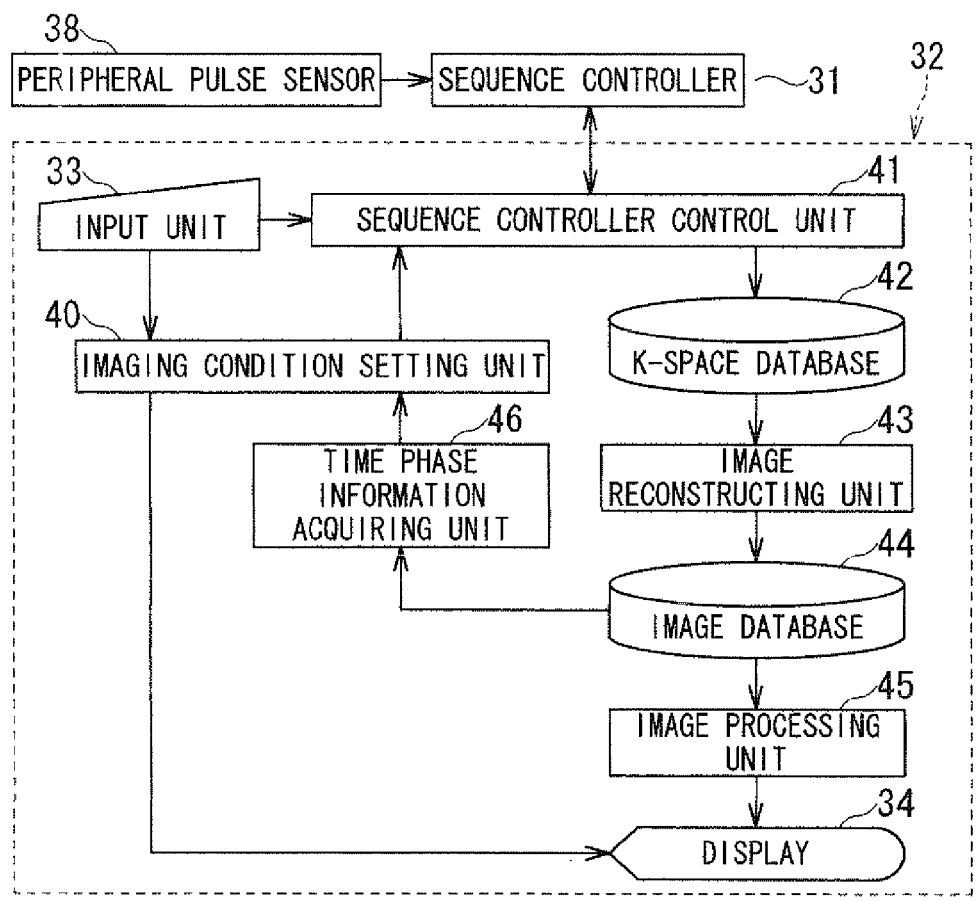
FIG. 2 is a functional block diagram of the computer shown in FIG. 1.

FIG. 2 is a functional block diagram of the computer 32 shown in FIG. 1.

The computer 32 functions, by a program, as an imaging condition setting unit 40, a sequence controller control unit 41, a k-space database 42, image reconstructing unit 43, image database 44, image processing unit 45, and time phase information acquiring unit 46.

The imaging condition setting unit 40 sets the imaging conditions, including a pulse sequence, based on the instruction information from the input unit 33, and sends the set imaging conditions to the sequence controller control unit 41. In addition, the imaging condition setting unit 40 sets the imaging conditions for blood flow speed measurement in sync with the PPG signal, and displays a setting screen on the display 34 for setting a delay time from a reference wave, such as an R wave in the ECG signal as an imaging condition to perform imaging in sync with the PPG signal.

When scan start instruction information from the input unit 33 is received, the sequence controller control unit 41 controls the sequence controller 31 by giving the sequence controller 31 the imaging conditions acquired from the imaging condition setting unit 40. The sequence controller control unit 41 also receives the raw data from the sequence controller 31, and arranges it into the k-space formed in the k-space database 42.

The image reconstructing unit 43 receives the k-space data from the k-space database 42 and reconstructs image data from the k-space data by performing image reconstruction processing including a Fourier transform (FT). Then, the image reconstructing unit 43 stores the reconstructed image data into the image database 44.

The image processing unit 45 fetches the image data from the image database 44, performs required image processing to generate two-dimensional image data for display, and displays the generated image data on display 34.

The time phase information acquiring unit 46 (an electro-cardio information acquisition unit or a cardiac beat information unit) receives phase image data acquired by the pulse sequence for measurement of the blood flow velocity from image database 44, and calculates temporal change of a blood flow velocity based on the phase image data.

The time phase information acquiring unit 46 also calculates a relative time difference between the reference point on a PPG signal and the reference point on an ECG signal based on the calculated temporal change of the flow velocity and the PPG signal. Further, the time phase information acquiring unit 46 calculates a time interval of two adjacent reference waves, such as two adjacent R waves of the ECG signal based on the temporal change of the blood flow velocity, or two adjacent PPG trigger signals of the PPG signal.

Then, the time phase information acquiring unit 46 sends the calculated the time interval of the reference waves and the relative time difference between the reference point on the PPG signal and the reference point on the ECG signal to the imaging condition setting unit 40.

(Operation and Effect)

Next, operation and effect of the magnetic resonance imaging apparatus 20 will be explained.

Figure 3:
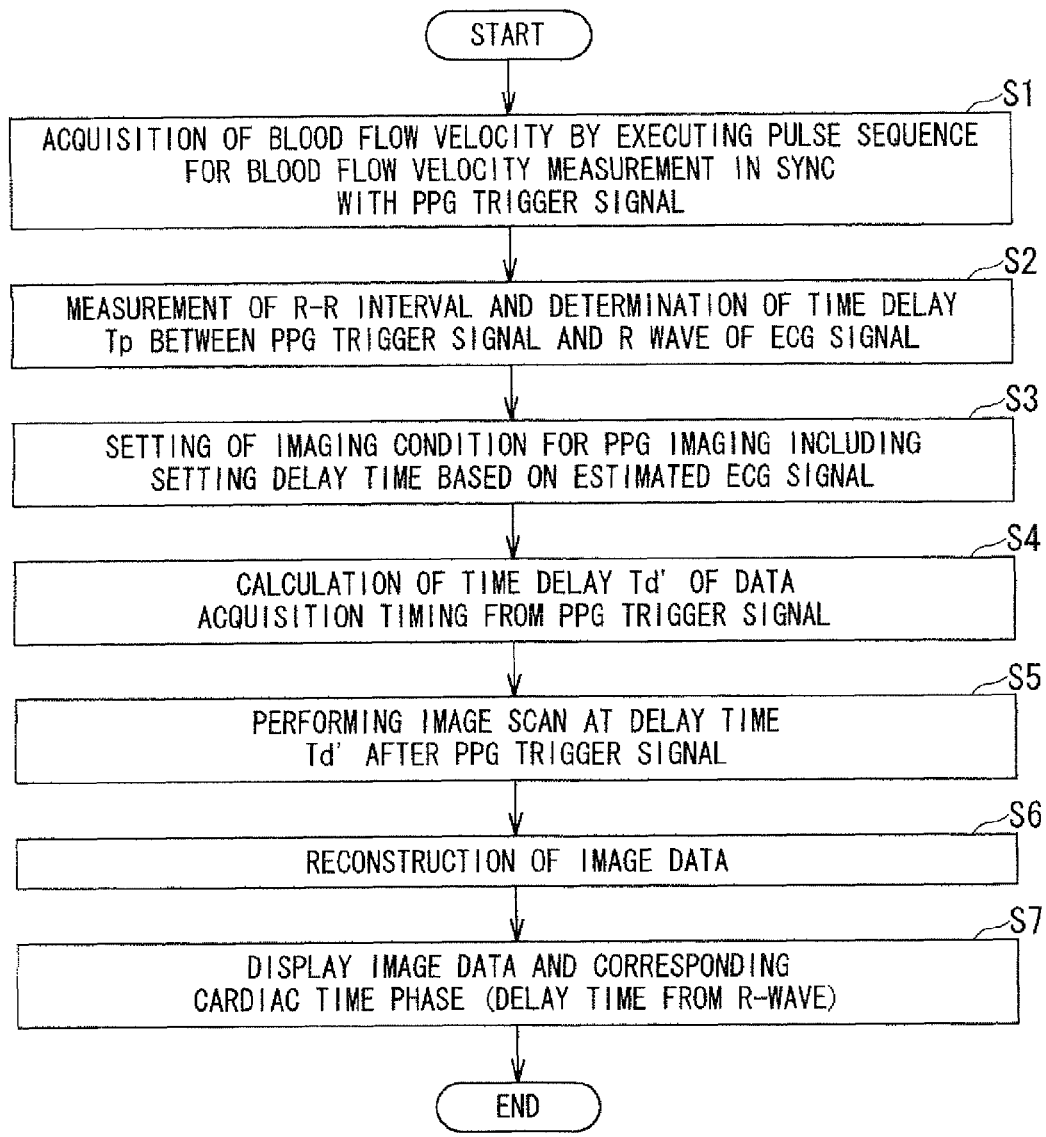
FIG. 3 shows a flow chart in which time phase information on the cardiac cycle is acquired using the PPG signal obtained from object P, and the images of a specific time phase of the cardiac cycle is acquired by the magnetic resonance imaging apparatus shown in FIG. 1.

FIG. 3 is a flow chart showing processes in which information on the time phase of the cardiac cycle is obtained using the PPG signal acquired from object P, and an image data of a specific time phase of the cardiac cycle are acquired.

In Step S1, a pulse sequence for blood flow velocity measurement is executed in sync with a PPG signal. Then, temporal change of a blood flow velocity is calculated using echo data acquired by the pulse sequence for blood flow velocity measurement.

Imaging conditions for the pulse sequence for the blood flow velocity measurement is preset in the imaging condition setting unit 40.

A pulse sequence for high speed cine imaging is preferred as a pulse sequence for blood flow velocity measurement from a viewpoint of performing data acquisition for a short time. In this pulse sequence, a segmented k-space method and a phase contrast (PC) method are used, for example.

The segmented k-space method is a high-speed imaging method in which a k-space is divided into some segments, and the k-space data is sequentially fetched in segment by segment. On the other hand, the PC method is a technique of measuring a blood flow velocity using the phase difference information of a spin.

Specifically, the imaging condition setting unit 40 sets up a pulse sequence, as an imaging condition, for alternately applying flow encoding gradient magnetic field pulses having reversed polarity with respect to each other in a measurement direction of the blood flow velocity and, and for acquiring echo data corresponding to plural time phases in a cardiac cycle. The imaging condition setting unit 40 also sets information regarding an instruction for acquiring the PPG signal.

In order to measure a blood flow velocity with high accuracy, it is suitable to set a measurement direction of the flow velocity to a cephalocaudal direction of the object P in which large flow velocity is obtained. It is also suitable to set an imaging cross section to a cross section which crosses a blood vessel.

Since the position of a heart can be verified on the coronal section image of the object P acquired by positioning imaging performed beforehand, position setting for imaging a cross section can be easily done. The set imaging condition is given to the sequence controller control unit 41 from the imaging condition setting unit 40.

Meanwhile, an object P is set to the bed 37 beforehand, and then, a static magnetic field is formed in the imaging region by the static-magnetic-field magnet 21 (superconducting magnet). The static magnetic field is uniformized by supplying current to the shim coil 22 from the shim coil power supply 28.

Then, when a scan start instruction is given to the sequence controller control unit 41 from input unit 33, the sequence controller control unit 41 sends the imaging conditions including the pulse sequence to the sequence controller 31. The sequence controller 31 drives the gradient magnetic field power supply 27, the transmitter 29, and the receiver 30 according to the pulse sequence to form a gradient magnetic field in the imaging region where the object P is set, while generating an RF signal to transmit it from the RF coil 24.

With this RF signal, the nuclear magnetic resonance inside the object P occurs and an NMR signal is generated. The NMR signal is received by the receiving RF coil 24, and is sent to the receiver 30. The receiver 30 generates raw data in response to the NMR signal from the RF coil 24 and sends the generated raw data to the sequence controller 31. The sequence controller 31 further sends the raw data to the sequence controller control unit 41.

The sequence controller control unit 41 arranges the raw data as k-space data into the k-space formed in the k-space database 42.

Meanwhile, during acquisition of data under control of the sequence controller 31, a PPG signal is outputted from the peripheral pulse sensor 38. The above mentioned acquisition and arrangement of the k-space data by execution of the pulse sequence are retrospectively performed synchronizing with the PPG signal. That is, the sequence controller control unit 41 generates a set of k-space data corresponding to plural different time phases of the cardiac cycle based on the PPG signal, and arranges the set of the generated k-space data into the k-space formed in the k-space database 42.

Next, the image reconstructing unit 43 acquires k-space data for each time phase of the cardiac cycle obtained by execution of the above-mentioned pulse sequence for blood flow velocity measurement from the k-space database 42. Then, the image reconstructing unit 43 reconstructs phase image data corresponding to plural different time phases of the cardiac cycle. The reconstructed phase image data is stored in the image database 44.

After that, the time phase information acquiring unit 46 acquires the phase image data corresponding to each different time phase of the cardiac cycle from the image database 44, and calculates temporal change of the blood flow velocity based on the phase image data. Using this temporal change of the blood flow velocity, a time delay of the data acquisition timing from the PPG signal can be determined. This time delay is suitable for acquiring data corresponding to a specific time phase of the cardiac cycle, as mentioned below.

Figure 4:
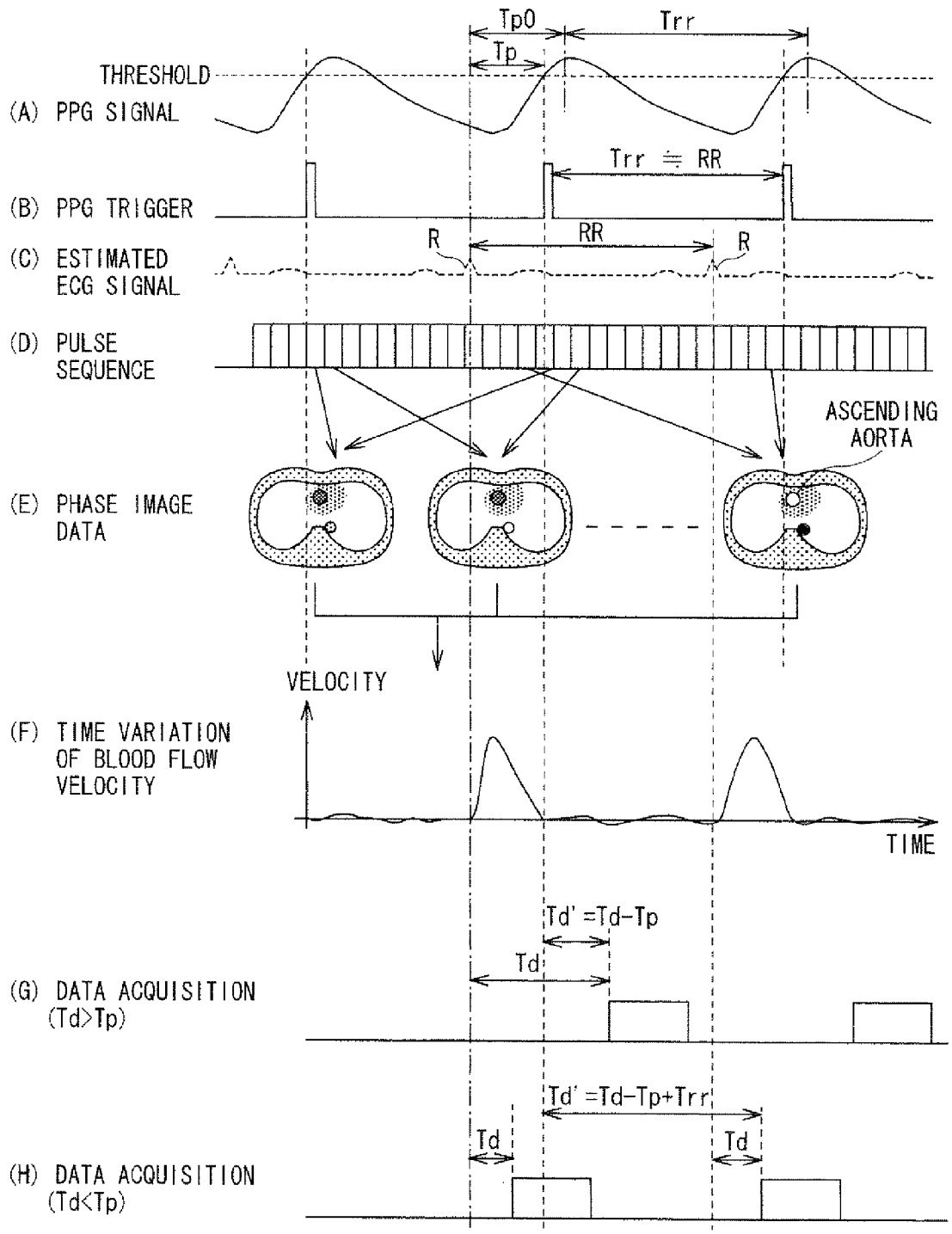
FIG. 4 is a figure explaining the calculating method of the temporal change of the blood flow velocity and a method of determining the time delay from a PPG signal, which are performed in the computer shown in FIG. 2.

FIG. 4 is a figure explaining a calculating method of the temporal change of the blood flow velocity and a determining method of the time delay from the PPG signal. Both methods are performed in computer 32. In FIGS. 4(A)-4(H), a horizontal axis shows time.

FIG. 4 (A) shows a PPG signal. By setting a threshold to a PPG signal, a trigger signal as shown in FIG. 4 (B) is generated as a signal for synchronization of the data acquisition.

FIG. 4 (C) shows an ECG signal including R waves as reference waves. In this embodiment, the ECG signal in itself is not actually used but is estimated. More specifically, a position of the R wave of the ECG signal is estimated from a result of the blood velocity measurement.

The PPG signal appears with a time delay from ventricular contraction, because the PPG signal is detected at a position apart from a heart. The time delay depends on conditions, such as distance between a heart and a detection position of the PPG signal, or hardness of a blood vessel.

It should be noted that an interval Trr of the PPG signal can be considered to be equal to an interval RR of the ECG signal, as shown in FIGS. 4(B) and 4(C), while the PPG signal is delayed by time delay Tp from the ECG signal. Therefore, if the time delay Tp can be estimated without using an ECG signal, it will become possible to match a certain time delay from the trigger signal generated from the PPG signal with a specific time phase of the cardiac cycle.

In order to estimate the time delay Tp, without using an ECG signal, the temporal change of the blood flow velocity in the pars ascendens aortae near the left ventricle is calculated as follows, for example.

FIG. 4 (D) shows a pulse sequence for measurement of the blood flow velocity. The pulse sequence for measurement of the blood flow velocity is executed repeatedly in sync with the trigger signal generated from the PPG signal. Specifically, whenever a trigger signal is detected, an amount of phase encoding is updated one by one. That is, within one interval, only a part of the entire amount of phase encoding necessary for reconstructing a full image data is acquired, and the entire amount of phase encoding is acquired from plural intervals of the trigger signal.

Meanwhile, data corresponding to plural time phase different from each other, while having the same amount of phase encoding, are acquired in one cardiac cycle. The acquisition of the data corresponding to plural time phases of the cardiac cycle is repeated until the data corresponding to all the amounts of phase encoding for filling k-space is acquired.

After the data corresponding to all the amounts of phase encoding is acquired, k-space data is rearranged by sequence controller control unit 41.

Then, plural sets of k-space data are obtained for respective time phase of the cardiac cycle. Each set corresponds to the same time phase of the cardiac cycle acquired in the different amount of phase encoding.

Then, phase image data for respective time phase of the cardiac cycle, as shown in FIG. 4 (E), are reconstructed from the k-space data for the respective time phase by the image reconstructing unit 43. More specifically, data acquisition using two flow encoding gradient magnetic fields, having an opposite polarity with respect to each other, is performed with the same time phase of the cardiac cycle and the same amount of phase encoding. As a result, two sets of complex data are obtained as k-space data. Then, subtraction of the two sets of complex data is performed to calculate the phase thereof for generating phase data. Further, by performing processing including Fourier transformation to the phase data, phase image data is obtained, as shown in FIG. 4(E).

A pixel value in the phase image data generated in this way shows a velocity of a corresponding pixel. Therefore, plural phase image data serves as a velocity map corresponding to respective time phase of the cardiac cycle.

Since a tissue other than a blood vessel has smaller motion velocity compared with the blood vessel, the pixel value becomes small.

Among blood vessels, the pars ascendens aortae have the highest blood flow velocity in a direction from the leg to the head of the object P in the axial cross section of object P. The pars ascendens aortae also show the highest velocity change rate during a cardiac cycle.

Therefore, the position and region of the pars ascendens aortae can be easily detected by processing such as a threshold processing, maximum extracting processing, or a differential processing.

The detection of the position and region of the pars ascendens aortae is performed by the time phase information acquiring unit 46. The time phase information acquiring unit 46 calculates an average of the blood flow velocity from the pixel value of plural pixels in the pars ascendens aortae. As shown in FIG. 4 (F), from the averaged blood flow velocity plotted in the direction of a time phase of the cardiac cycle, the temporal change of the blood flow velocity (cm/s) is obtained. Since the pars ascendens aortae are near the heart of an object, it is thought that the flow velocity of the pars ascendens aortae synchronizes with the cardiac beat of the heart without delay. Therefore, it can be considered that a change point, at which the blood flow velocity rises from an approximately zero velocity, is the timing of the R wave of an ECG signal.

Next, in Step S2, the time phase information acquiring unit 46 measures an R-R interval and determines a time delay Tp between the trigger signal generated from the PPG signal and the R wave.

The R-R interval can be measured based on the trigger signal, or temporal change of or a blood flow velocity. That is, The R-R interval can be obtained simply and with high accuracy by measuring a time interval Trr of two adjacent trigger signals.

Alternatively, the R-R interval can be also obtained by extracting periodic distinguishable points from the temporal change of the blood flow velocity, and by measuring the interval of the two adjacent distinguishable points.

Further, by averaging plural time intervals Trr, an accurate R-R interval can be obtained.

On the other hand, as mentioned above, time delay Tp from the R wave to the PPG trigger signal can be determined by estimating that a time point where blood flow velocity of the pars ascendens aortae changes most significantly toward a positive side is a position of the R wave, and by measuring a period from the estimated R wave to the subsequent PPG trigger signal.

It should be noted that the time delay Tp of the PPG trigger signal from the R wave is a period from the R wave to a time at which the signal value of a PPG signal exceeds a threshold to generate a trigger signal, and does not necessarily coincide with Tp0, which is a period from the R wave to the peak of the PPG signal, as shown in FIG. 4(A).

The R-R interval and the time delay Tp of the PPG trigger signal from the R wave, obtained in the above mentioned manner, are sent to the imaging condition setting unit 40 from the time phase information acquiring unit 46.

Next, in Step S3, the imaging condition setting unit 40 sets the imaging condition for acquiring image data of the specific time phase of the cardiac cycle by imaging in sync with the PPG signal. For this purpose, the imaging condition setting unit 40 displays a screen for setting the imaging condition on the display 34.

Figure 5:
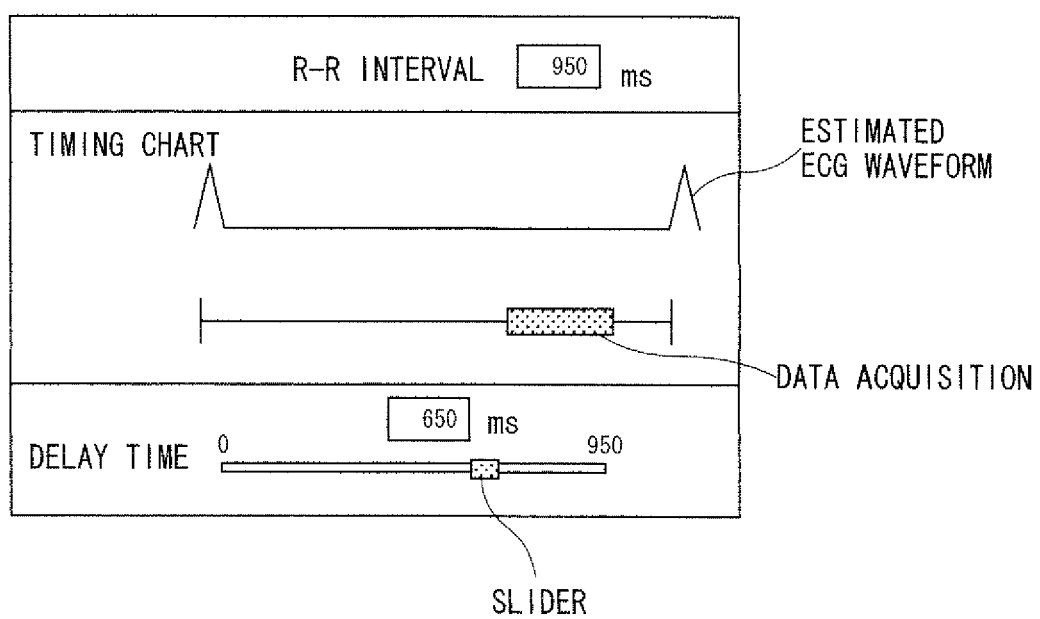
FIG. 5 is a figure showing an example of a screen for setting the time delay from the R wave for PPG imaging displayed on the display shown in FIG. 1.

FIG. 5 is a figure showing an example of the screen on display 34 for setting the time delay from the R wave, which is necessary for PPG imaging.

The data acquisition timing in PPG imaging can be set using the time delay Td from an R wave, via a user interface as shown in FIG. 5. Thus, the timing chart which shows an estimated ECG waveform having the obtained R-R interval and an indication figure of the data acquiring period in the pulse sequence is displayed as reference information on the screen.

The obtained R-R interval may be numerically displayed on the screen.

Seeing the display on the screen, a user can set time delay Td from the R wave corresponding to a specific time phase of the cardiac cycle with a substantially the same operation as one for the usual imaging in sync with the ECG signal. The user may input the time delay Td from the R wave by inputting numerals or moving a slider using the input device 33.

Next, in S4, the imaging condition setting unit 40 calculates a time delay Td' of the data acquisition timing from the PPG trigger signal in an actual imaging, based on the inputted time delay Td from the R wave, and previously determined time delay Tp of the PPG trigger signal from the R wave.

That is, the time delay Td' of the data acquisition timing from the PPG trigger signal corresponding to the time delay Td from the R wave is calculated.

When Td inputted by the user is longer than the time delay Tp of the PPG trigger signal from the R wave, (i.e., Td>Tp), the time delay Td' of the data acquisition timing from the PPG trigger signal can be calculated by the following equation (1).

$$Td' = Td - Tp \tag{1}$$

Namely, since the PPG trigger signal is delayed by the time delay Tp from the R wave, as shown in FIG. 4 (G), the time delay Td' coincides with a time that the time delay Tp is subtracted from the time delay Td.

On the other hand, when Td inputted by the user is shorter than the time delay Tp of the PPG trigger signal from the R wave, (i.e., Td<Tp), the time delay Td' of the data acquisition timing from a PPG trigger signal can be calculated by the following equation (2).

$$Td' = Td - Tp + Trr \tag{2}$$

In this case, the time delay Td' of the data acquisition timing from the PPG trigger signal may be determined so that data is acquired in the next cardiac cycle of the cardiac cycle, as shown in FIG. 4 (H).

Next, in Step S5, imaging condition setting unit 40 performs an image scan in sync with the PPG signal, using the calculated time delay Td' of the data acquisition timing from the PPG trigger signal as a control condition.

Specifically, together with the pulse sequence for imaging scan set in the imaging condition setting unit 40, the time delay Td' of the data acquisition timing from a PPG trigger signal is outputted to the sequence controller 31 through the sequence controller control unit 41 as a control condition. The sequence controller 31 generates a PPG trigger signal as a signal for synchronization at a time when the PPG signal acquired by the peripheral pulse sensor 38 exceeds the threshold.

Then, the sequence controller 31 controls gradient magnetic field power supply 27, transmitter 29, and receiver 30 so that data acquisition is performed after the time delay Td' from the PPG trigger signal.

This data acquisition is equivalent to the data acquisition after the time delay Td from the R wave. Then, in a manner similar to the data acquisition by execution of the pulse sequence for blood flow velocity measurement, k-space data acquired by the pulse sequence for imaging is arranged into the k-space in the k-space database 42.

Next, in Step SE, the image reconstructing unit 43 reads out the k-space data from the k-space database 42, and reconstructs image data. The reconstructed image data is stored in the image database 44.

In Step S7, the image processing unit 45 fetches the image data from the image database 44, performs necessary image processing to generate two-dimensional image data for display, and displays the generated image data on the display 34. On displaying the image data, the imaging condition setting unit 40 may further displays the time delay Td from the R wave corresponding to the displayed image data on the display 34 as additional information. This additional information on the image data may also be stored in the image database 44, while being associated with the image data.

Accordingly, the user can set a time delay from a reference wave, such as an R wave of an ECG signal as data acquisition timing without actually acquiring an ECG signal from object P, and can refer to the image data corresponding to a desired time phase of the cardiac cycle.

As mentioned above, the magnetic resonance imaging apparatus 20 obtains a time difference between a reference point on the ECG signal and a reference point on the PPG signal, based on the PPG signal and a temporal change of the flow velocity which is obtained by executing the pulse sequence for blood flow velocity measurement under synchronization with the PPG signal. Further, the magnetic resonance imaging apparatus 20 specifies the time phase of the cardiac cycle of the image data acquired by a PPG imaging (i.e., a imaging in sync with the PPG signal), by using a reference wave interval, such as R-R interval obtained from the temporal change of the blood flow velocity, or the PPG signal, and the time difference between a reference point on the ECG signal and a reference point on the PPG signal.

The above mentioned data acquisition for imaging at Step S5 is performed after the time delay Td' from a PPG trigger signal, and therefore, it is what is called a prospective data acquisition.

By contrast, retrospective data acquisition based on the PPG signal may be performed. In the retrospective data acquisition, in Step S5, plural sets of the k-space data which correspond to all the time phase of the cardiac cycles are acquired based on the PPG signal. Then, in Step S6, k-space data corresponding to the specific time phase of the cardiac cycle after the time delay Td' from the PPG trigger signal is extracted out of the acquired plural sets of the k-space data, and image reconstruction is performed using the extracted k-space data.

As mentioned above, according to the embodiment of the magnetic resonance imaging apparatus 20, an image corresponding to a desired time phase of the cardiac cycle can be acquired, without acquiring an ECG signal from an object. Therefore, an unstable synchronization by disorder of the ECG signal resulting from the application of the gradient magnetic field, and time and effort needed for attaching the ECG electrode to the object are avoided. There is also no problem regarding heat generation of the ECG electrode in a high magnetic field MRI apparatus.

In addition, data acquisition timing can be set as a time delay from reference wave, such as an R wave of the ECG signal, without actually using the ECG signal, in a simple manner similar to imaging condition setting for a conventional imaging in sync with the ECG signal.

(Modification)

According to the embodiment mentioned above, in order to estimate the position of the reference wave, such as an R wave, on the ECG signal, the temporal change of the blood flow velocity of the pars ascendens aortae is measured. However, as long as the position of the reference wave on an ECG signal can be estimated, other human biomedical information may be used.

For example, blood flow velocity projection data of the section containing an aorta acquired without applying an encoding phase, cross-sectional area of a ventricle, or projection data of a ventricle shape may be used as human biomedical information for estimating the position of the reference wave on an ECG signal.

Further, not only the PPG signal but also arbitrary biomedical signals other than an FOG signal showing a cardiac beat can be used. For example, a cardiac sound signal or a vibration signal caused by a heart beat can be used for synchronization in a manner similar to the PPG signal.

As mentioned above, when displaying image data, by displaying a corresponding time phase of the cardiac cycle as additional information, the user can easily verify the time phase of the cardiac cycle of the displayed image data. When plural image data corresponding to plural time phases of the cardiac cycles are stored in the image database 44, an image data corresponding to a desired specific time phase can be selected to display among the plural image data, using the additional information on the time phase of the cardiac cycle.

While certain embodiments have been described, these embodiments have been presented by way of example only, and are not intended to limit the scope of the invention. Indeed, the novel apparatuses and units described herein may be embodied in a variety of other forms; furthermore, various omissions, substitutions and changes in the form of the apparatuses and units described herein may be made without departing from the spirit of the invention. The accompanying claims and their equivalents are intended to cover such forms or modifications as would fall within the scope and spirit of the invention.

What is claimed is:

1. A magnetic resonance imaging apparatus, comprising:
   (a) an electrocardio information acquisition unit configured to acquire a magnetic resonance signal and use it to estimate an electrocardiogram signal of an object in sync with a biomedical signal other than an electrocardiogram signal, the biomedical signal being acquired from the object and showing a cardiac beat, and
   (b) to determine a time difference between a position of a reference wave of the estimated electrocardiogram signal and a synchronous position of the biomedical signal, the position of the reference wave being estimated from the acquired magnetic resonance signal; and
   (c) an image data generation unit configured to acquire a magnetic resonance signal for imaging corresponding to a specific time phase of the cardiac cycle in sync with the biomedical signal based on the time difference, and
   (d) to generate an image data corresponding to the specific time phase of the cardiac cycle from the acquired magnetic resonance signal for imaging.

2. The magnetic resonance imaging apparatus according to claim 1, wherein,
   the biomedical signal is a peripheral pulse signal.

3. The magnetic resonance imaging apparatus according to claim 2, wherein,
   said electrocardio information acquisition unit acquires the magnetic resonance signal for estimating the electrocardiogram signal of the object using a phase contrast method to obtain an aortic blood flow velocity, determines the position of the reference wave of the electrocardiogram signal from the aortic blood flow velocity, and further determines the time difference from the determined position of the reference wave of the electrocardiogram signal and the synchronous position of the peripheral pulse signal.

4. The magnetic resonance imaging apparatus according to claim 2, wherein,
   said image data generation unit converts a time delay from the reference wave of the electrocardiogram signal which is set as imaging condition into a time delay from the synchronous position of the peripheral pulse signal, based on the time difference, and acquires the magnetic resonance signal for imaging after the time delay from the synchronous position of the peripheral pulse signal.

5. The magnetic resonance imaging apparatus according to claim 2, further comprising a reference information displaying unit, wherein,
   said electrocardio information acquisition unit further determines an interval of the reference wave on the electrocardiogram signal using the peripheral pulse signal, and
   said reference information displaying unit displays the interval of the reference wave on the electrocardiogram signal as reference information for setting the time delay from the reference wave of the electrocardiogram signal as an imaging condition.

6. The magnetic resonance imaging apparatus according to claim 2, further comprising a reference information displaying unit, wherein,
   said electrocardio information acquisition unit further determines an interval of the reference wave on the electrocardiogram signal using the magnetic resonance signal for estimating the electrocardiogram signal of the said object, and
   said reference information displaying unit displays the interval of the reference wave on the electrocardiogram signal as reference information for setting the time delay from the reference wave of the electrocardiogram signal as an imaging condition.

7. The magnetic resonance imaging apparatus according to claim 2, wherein,
   said image data generation unit adds information as additional information which shows the specific time phase of the cardiac cycle to the image data corresponding to the specific time phase of the cardiac cycle.

8. A magnetic resonance imaging apparatus, comprising:
   (a) an electrocardio information acquisition unit configured to acquire a magnetic resonance signal and use it to estimate an electrocardiogram signal of an object in sync with a biomedical signal other than an electrocardiogram signal, the biomedical signal being acquired from the object and showing a cardiac beat, and
   (b) to determine a time difference between a position of a reference wave of the estimated electrocardiogram signal and a synchronous position of the biomedical signal, the position of the reference wave being estimated from the acquired magnetic resonance signal; and (c) an image data generation unit configured to acquire magnetic resonance signals for imaging in sync with the biomedical signal, (d) to extract a magnetic resonance signal corresponding to a specific time phase of the cardiac cycle from the acquired magnetic resonance signals for imaging, based on the time difference, and (e) to generate an image data corresponding to the specific time phase of the cardiac cycle from the extracted magnetic resonance signal.

9. The magnetic resonance imaging apparatus according to claim 8, wherein, the biomedical signal is a peripheral pulse signal.

10. A magnetic resonance imaging apparatus, comprising: a cardiac beat information acquisition unit configured (a) to acquire, in sync with a first signal showing a cardiac beat and acquired from the object, a magnetic resonance signal for estimating a reference position of a second signal also showing a cardiac beat, and (b) to determine a time difference between the reference position of the second signal and a synchronous position of the first signal, the reference position of the second signal being estimated from the acquired magnetic resonance signal; and (c) an image data generation unit configured to acquire a magnetic resonance signal for imaging corresponding to a specific time phase of the second signal in sync with the first signal based on the time difference, and (d) to generate an image data corresponding to the specific time phase of the second signal from the acquired magnetic resonance signal for imaging.

* * * * *